United States Patent [19]
Voris et al.

[11] Patent Number: 6,099,850
[45] Date of Patent: Aug. 8, 2000

[54] TERMITE AND BORING INSECT BARRIER FOR THE PROTECTION OF WOODEN STRUCTURES

[75] Inventors: Peter Van Voris, Richland; Dominic A. Cataldo, Kennewick, both of Wash.; Frederick G. Burton, Stansbury Park, Utah; Norman R. Gordon, Kennewick, Wash.; Joel R. Coats, Ames, Iowa; W. Eugene Skiens, Wilsonville, Oreg.

[73] Assignee: Battelle Memorial Institute, Richland, Wash.

[21] Appl. No.: 08/482,151

[22] Filed: Jun. 7, 1995

Related U.S. Application Data

[63] Continuation-in-part of application No. 08/348,774, Dec. 1, 1994, abandoned, which is a continuation of application No. 08/117,877, Sep. 7, 1993, abandoned, which is a continuation of application No. 07/893,970, Jun. 4, 1992, abandoned, which is a continuation of application No. 07/401,955, Sep. 1, 1989, abandoned, which is a continuation-in-part of application No. 06/555,113, Nov. 23, 1983, Pat. No. 5,116,414, which is a continuation-in-part of application No. 06/314,809, Oct. 26, 1981, abandoned, and application No. 06/314,810, Oct. 26, 1981, abandoned.

[51] Int. Cl.[7] .......................... A01N 25/34; A01N 37/34; A01N 53/02; A01N 57/02
[52] U.S. Cl. ................................. 424/411; 424/DIG. 11; 514/124; 514/521; 514/531
[58] Field of Search ............................. 514/59, 124, 521, 514/531; 504/116; 71/DIG. 1; 424/411, DIG. 11

[56] References Cited

U.S. PATENT DOCUMENTS

| | | | |
|---|---|---|---|
| Re. 32,356 | 2/1987 | Cardarelli | 424/78 |
| 1,999,458 | 4/1935 | Hollister | 47/1 |
| 2,970,404 | 2/1961 | Beaufils et al. | 47/57.5 |
| 3,111,403 | 11/1963 | Soper | 71/2.3 |

(List continued on next page.)

FOREIGN PATENT DOCUMENTS

| | | |
|---|---|---|
| 23427/84 | 8/1984 | Australia . |
| 48655/90 | 8/1990 | Australia . |
| 62329/90 | 3/1991 | Australia . |
| 91/82443 | 8/1991 | Australia . |
| 82443/91 | 2/1992 | Australia ....................... A01N 25/10 |
| 95/13886 A1 | 8/1995 | Australia . |
| 52454/96 | 12/1996 | Australia . |
| 2 070 231 | 12/1992 | Canada . |
| 0 286 009 A2 | 10/1988 | European Pat. Off. .......... B27K 3/50 |
| 0 594 892 | 5/1994 | European Pat. Off. . |
| 77 72802 | 6/1977 | Japan .............................. B27K 3/34 |
| 58-39601 | 3/1983 | Japan . |
| 86/1133 | 2/1986 | South Africa . |
| 2 018 593 | 10/1979 | United Kingdom . |
| 2 098 541 | 11/1982 | United Kingdom . |
| WO 84/02447 | 7/1984 | WIPO ............................ A01N 25/34 |
| WO 90/14004 | 11/1990 | WIPO . |
| WO 95/18532 | 7/1995 | WIPO ............................ A01N 25/34 |
| WO 97/47190 | 12/1997 | WIPO . |

OTHER PUBLICATIONS

Batelle Technology Transfer Bulletin, "Controlled–Release Chemicals for Inhibiting Plant Roots," 2 pgs. (Dec. 1984).

Cline et al., "Biobarriers used in Shallow Burial Ground Stabilization," *Nuclear Technology*, vol. 58, pp. 150–153 (1982).

Hughes, "Controlled Release Technology Inhibits Root Growth," *Controlled Release*, p. 15.

Jury et al., "Behaviour Assessment Model for Trace Organics in Soil: I. Model Description," *J. Environ. Qual.*, vol. 12, No. 4, pp. 558–564 (1983).

(List continued on next page.)

*Primary Examiner*—S. Mark Clardy
*Attorney, Agent, or Firm*—Arnold White & Durkee

[57] ABSTRACT

A method and device are disclosed which prevent the intrusion of insects onto wood structures by using a controlled release device capable of releasing insecticide. In the disclosed method, the device maintains a minimal effective level of insecticide for a predetermined period of time.

11 Claims, 5 Drawing Sheets

U.S. PATENT DOCUMENTS

| | | | |
|---|---|---|---|
| 3,257,190 | 6/1966 | Soper | 71/2.3 |
| 3,367,065 | 2/1968 | Cravens | 47/57.5 |
| 3,502,458 | 3/1970 | Schenk | 71/64 |
| 3,592,792 | 7/1971 | Newland et al. | 260/41 |
| 3,608,062 | 9/1971 | Alfes et al. | 424/22 |
| 3,639,583 | 2/1972 | Cardarelli et al. | 424/125 |
| 3,671,548 | 6/1972 | Itaya et al. | 549/79 |
| 3,691,683 | 9/1972 | Sterzik | 47/57.5 |
| 3,705,938 | 12/1972 | Hyman et al. | 424/19 |
| 3,706,161 | 12/1972 | Jenson | 47/57.5 |
| 3,716,560 | 2/1973 | Taya et al. | 549/471 |
| 3,759,941 | 9/1973 | Sampei et al. | 548/117 |
| 3,835,176 | 9/1974 | Matsuo et al. | 558/407 |
| 3,835,220 | 9/1974 | Matsui et al. | 424/40 |
| 3,846,500 | 11/1974 | Kitamura et al. | 568/660 |
| 3,851,053 | 11/1974 | Cardarelli | 424/78 |
| 3,857,934 | 12/1974 | Bernstein et al. | 424/30 |
| 3,864,114 | 2/1975 | Green | 71/3 |
| 3,864,388 | 2/1975 | Kitamura et al. | 560/60 |
| 3,867,542 | 2/1975 | Ueda et al. | 514/461 |
| 3,876,681 | 4/1975 | Okuno et al. | 560/124 |
| 3,880,643 | 4/1975 | Cooke et al. | 71/78 |
| 3,891,423 | 6/1975 | Stanley et al. | 71/86 |
| 3,899,586 | 8/1975 | Okuno et al. | 514/417 |
| 3,906,089 | 9/1975 | Okuno et al. | 424/45 |
| 3,954,814 | 5/1976 | Mizutani et al. | 549/449 |
| 3,966,963 | 6/1976 | Okuno et al. | 514/531 |
| 3,970,703 | 7/1976 | Kitamura et al. | 568/662 |
| 3,981,903 | 9/1976 | Hirano et al. | 560/124 |
| 3,998,868 | 12/1976 | Mitzutani et al. | 560/124 |
| 4,003,945 | 1/1977 | Kitamura et al. | 560/124 |
| 4,007,258 | 2/1977 | Cohen et al. | 424/22 |
| 4,021,122 | 5/1977 | Krenmayr | 356/240 |
| 4,037,352 | 7/1977 | Hennart et al. | 43/129 |
| 4,063,919 | 12/1977 | Grano, Jr. | 71/11 |
| 4,065,555 | 12/1977 | Potter | 424/83 |
| 4,077,795 | 3/1978 | Cooke et al. | 71/78 |
| 4,082,533 | 4/1978 | Wittenbrook et al. | 71/28 |
| 4,102,991 | 7/1978 | Kydonieus | 424/27 |
| 4,104,374 | 8/1978 | Reuther et al. | 424/185 |
| 4,118,505 | 10/1978 | Kitamura et al. | 514/438 |
| 4,123,250 | 10/1978 | Kupelian | 71/78 |
| 4,160,335 | 7/1979 | Von Kohorn et al. | 43/131 |
| 4,172,904 | 10/1979 | Young et al. | 427/4 |
| 4,176,189 | 11/1979 | Itaya et al. | 514/389 |
| 4,190,680 | 2/1980 | Young et al. | 427/4 |
| 4,193,984 | 3/1980 | Kydonieus | 424/16 |
| 4,198,441 | 4/1980 | Young et al. | 427/2 |
| 4,198,782 | 4/1980 | Kydonieus et al. | 47/58 |
| 4,200,664 | 4/1980 | Young et al. | 427/4 |
| 4,205,096 | 5/1980 | Young et al. | 427/4 |
| 4,212,879 | 7/1980 | Ohsumi et al. | 514/427 |
| 4,229,469 | 10/1980 | Mizutani et al. | 514/519 |
| 4,235,872 | 11/1980 | Tocker | 424/19 |
| 4,237,113 | 12/1980 | Cardarelli | 424/78 |
| 4,237,114 | 12/1980 | Cardarelli | 424/78 |
| 4,260,626 | 4/1981 | Carr et al. | 424/273 R |
| 4,263,463 | 4/1981 | Kitamura et al. | 568/873 |
| 4,269,626 | 5/1981 | Gorke et al. | 106/18.32 |
| 4,272,520 | 6/1981 | Kydonieus et al. | 424/84 |
| 4,279,924 | 7/1981 | Suzuki et al. | 514/521 |
| 4,282,207 | 8/1981 | Young et al. | 424/78 |
| 4,282,209 | 8/1981 | Tocker | 424/81 |
| 4,293,504 | 10/1981 | Suzuki et al. | 558/354 |
| 4,320,113 | 3/1982 | Kydonieus | 424/27 |
| 4,327,109 | 4/1982 | Mizutani et al. | 514/443 |
| 4,336,194 | 6/1982 | Ohsumi et al. | 548/562 |
| 4,344,250 | 8/1982 | Fahlstrom | 47/57.5 |
| 4,348,218 | 9/1982 | Bond, Jr. | 71/1 |
| 4,350,678 | 9/1982 | Palvarini et al. | 424/27 |
| 4,352,833 | 10/1982 | Young et al. | 427/4 |
| 4,360,376 | 11/1982 | Koestler | 71/121 |
| 4,374,126 | 2/1983 | Cardarelli et al. | 424/81 |
| 4,376,785 | 3/1983 | Matsuo et al. | 514/521 |
| 4,377,675 | 3/1983 | Daudt et al. | 528/25 |
| 4,400,374 | 8/1983 | Cardarelli | 424/78 |
| 4,405,360 | 9/1983 | Cardarelli | 71/117 |
| 4,435,383 | 3/1984 | Wysong | 424/78 |
| 4,457,929 | 7/1984 | Kamachi et al. | 424/246 |
| 4,496,586 | 1/1985 | Matsui et al. | 514/531 |
| 4,500,337 | 2/1985 | Young et al. | 71/67 |
| 4,500,338 | 2/1985 | Young et al. | 71/67 |
| 4,500,339 | 2/1985 | Young et al. | 71/67 |
| 4,503,071 | 3/1985 | Hirano et al. | 514/521 |
| 4,508,568 | 4/1985 | Fox | 106/2 |
| 4,576,801 | 3/1986 | Parry et al. | 427/288 |
| 4,579,085 | 4/1986 | McGuire | 119/156 |
| 4,639,393 | 1/1987 | Von Kohorn et al. | 428/304.4 |
| 4,666,706 | 5/1987 | Farquharson et al. | 424/408 |
| 4,666,767 | 5/1987 | Von Kohorn et al. | 428/304.4 |
| 4,680,328 | 7/1987 | Dohrer et al. | 524/137 |
| 4,747,902 | 5/1988 | Saitoh | 151/244.11 |
| 4,767,812 | 8/1988 | Chapin et al. | 524/144 |
| 4,808,454 | 2/1989 | Saitoh | 428/40.6 |
| 4,818,525 | 4/1989 | Kamada et al. | 424/81 |
| 4,842,860 | 6/1989 | Suguira et al. | 424/403 |
| 4,886,656 | 12/1989 | Obayashi et al. | 514/144 |
| 4,921,703 | 5/1990 | Higuchi et al. | 424/419 |
| 4,929,497 | 5/1990 | Mitchell et al. | 428/265 |
| 5,019,998 | 5/1991 | Cowen et al. | 364/496 |
| 5,104,659 | 4/1992 | Fishbein et al. | 424/411 |
| 5,116,414 | 5/1992 | Burton et al. | 71/121 |
| 5,135,744 | 8/1992 | Alexander et al. | 424/409 |
| 5,139,566 | 8/1992 | Zimmerman | 71/121 |
| 5,181,952 | 1/1993 | Burton et al. | 504/347 |
| 5,201,925 | 4/1993 | Itzel et al. | 47/58 |
| 5,292,504 | 3/1994 | Cardin et al. | 514/65 |
| 5,296,227 | 3/1994 | Norval et al. | 424/411 |
| 5,317,834 | 6/1994 | Anderson | 47/48.5 |
| 5,439,924 | 8/1995 | Mills | 514/345 |
| 5,449,250 | 9/1995 | Burton et al. | 405/128 |
| 5,492,696 | 2/1996 | Price et al. | 424/417 |

OTHER PUBLICATIONS

Jury et al., "Behaviour Assessment Model for Trace Organics in Soil: III. Application of Screening Model," *J. Environ. Qual.*, vol. 13, No. 4, pp. 573–579 (1984).

Jury et al., "Behaviour Assessment Model for Trace Organics in Soil: IV. Review of Experimental Evidence," *J. Environ. Qual.*, vol. 13, No. 4 (1984).

Roseman et al., "Chapter 18: The Use of Controlled Release Herbicides in Waste Burial Sites," *Controlled Release Delivery Systems* Marcel Dekker, NY (1983).

"Soil Fumigants are Remarkably Effective in Stopping Decay of Wood," *Chemical Week*, p. 39, (Sep. 25, 1974). *Abstract.

Solie et al., "Simulation of Trifluralin Diffusion in the Soil," *Transactions of the ASAE*, pp. 1463–1467 (1984).

Steyaart, "Proceedings, Eighty–Second Annual Meeting of the American Wood–Preservers' Association: Address," *Crossties*, vol. 68, No. 3, pp. 45–46 (1987).

Streile, "The Effect of Temperature on Pesticide Phase Partitioning, Trasnport, and Volatilization from Soil," *Abstract of the Dissertation*, (1984), 37 pages.

Van Voris et al., "Long–Term Controlled Release of Herbicides: Root–Growth–Inhibiting Biobarrier Technology," 19 pages.

Burton, et al., "A Controlled–Release Herbicide Device for Multiple–Year Control of Roots at Waste Burial Sites," *J. of Controlled Release* (1985), 8 pages.

Chang, et al., "Control of Ant Damage to Polyethylene Tubes Used in Drip Irrigation Systems in Hawaiian Sugarcane Fields," *International Society of Sugar Cane Technologists* (Feb. 1–11, 1980), pp. 1686–1692.

Chen, et al., "Approaches to the Improvement of Biological Resistance of Wood through Controlled Release Technology," *Proceedings of the 13th Int'l Symposium on Controlled Release of Bioactive Materials* (Aug. 3–6, 1986), pp. 75–76.

Kumar, et al., "The effect . . . treated wood," *J. Timber Dev. . . . India* (1977), 23(3), pp. 9–13.

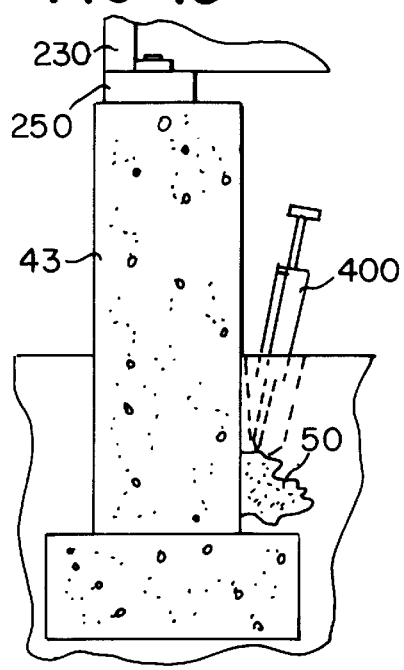
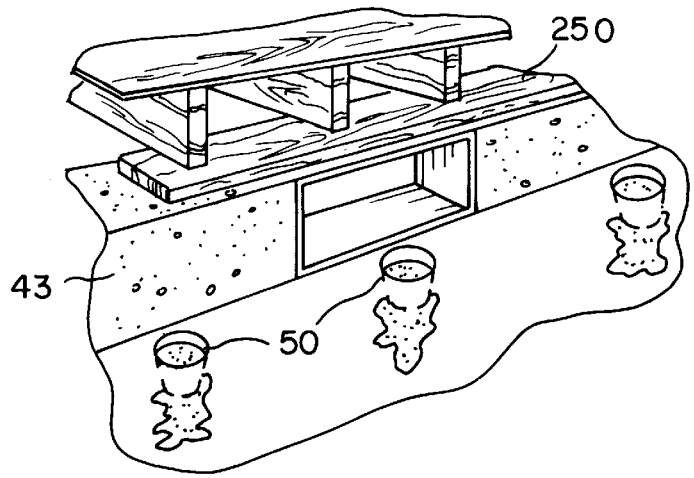
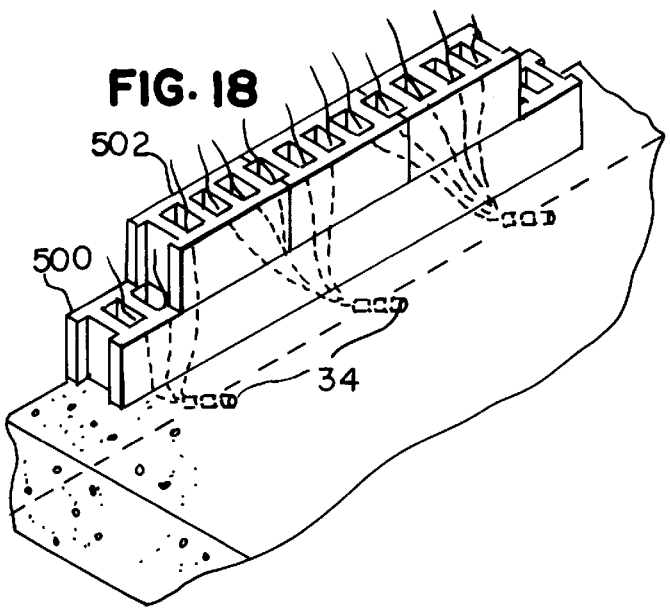
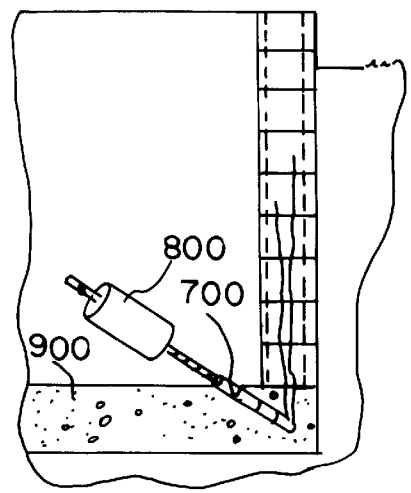

TERMITE AND BORING INSECT BARRIER FOR THE PROTECTION OF WOODEN STRUCTURES

CROSS REFERENCE TO RELATED APPLICATIONS

The present application is a Continuation-in-Part of U.S. patent application Ser. No. 08/348,774 filed on Dec. 1, 1994, which abandoned, is a continuation of U.S. patent application Ser. No. 08/117,877 filed on Sep. 7, 1993, now abandoned, which is a continuation of U.S. patent application Ser. No. 07/893,970 filed on Jun. 4, 1992, abandoned, which is a continuation of U.S. patent application Ser. No. 07/401,955 filed on Sep. 1, 1989, abandoned, which is a continuation-in-part of U.S. patent application Ser. No. 06/555,113 filed on Nov. 23, 1983, now U.S. Pat. No. 5,116,414, which is a continuation-in-part of U.S. patent application Ser. Nos. 06/314,809 and 06/314,810, both filed on Oct. 26, 1981 and now abandoned.

BACKGROUND OF THE INVENTION

The present invention relates to termite and boring insect barriers for the long-term protection of wooden structures. More particularly, it relates to a composition and method which creates and maintains an exclusion zone for insect pests such as termites, ants and other boring insects.

Wood which is in contact with concrete, such as in wooden building construction and wood which is in contact with soil for example fence posts, utility poles, railroad cross-ties and wooden supports, can be structurally degraded by the action of termites, ants and other boring insects. Insecticides are available to protect wood from the action of such pests.

Although insecticides are somewhat effective against the action of the boring insects, if insecticides are applied by themselves in sufficient quantity to be effective over a period of time, they pose ecological concerns, human health, and may present unpleasant odors, soil leaching and volatility of the insecticide. Furthermore, even the greatest amounts of insecticides applied by themselves dissipate within a relatively short time and need to be reapplied.

A further disadvantage of conventional application methods is that the concentration of active ingredients resulting from a single application of insecticide starts out well above the minimum level necessary for effectiveness, but decreases rapidly and within a relatively short period of time drops below the minimal effective level necessary for a barrier.

To this end, a number of techniques for the controlled release of chemicals such as insecticides have become common in recent years. These methods employ polymer matrices and microcapsules to release insecticide.

Cardarelli U.S. Pat. No. 4,400,374 discloses the use of polymer matrices generally made of polyethylene, polypropylene, ethylene vinyl acetate, polyamide, polystyrene, polyvinyl acetate, or polyurethane to control the release of insecticides such as the insecticide commercially available under the tradename Dursban. The polymer matrices disclosed in U.S. Pat. No. 4,400,374, incorporate porosigen and a porosity reducing agent which upon contact with soil moisture or an aqueous environment dissolves the matrix.

Similarly, Caraderelli U.S. Pat. No. 4,405,360 relates to a polymer release matrix which can be composed of polyamide, polyurethane, polyethylene, polypropylene, polystyrenes and other polymers. The control release mechanism works in combination with a porosigen to release a herbicide in a moist environment.

In addition, Wysong U.S. Pat. No. 4,435,383 teaches the use of a controlled release mechanism for insecticides including carbamates, organothiophosphates, organophosphates, perchlorinated organics and synthetic pyrethroids. The release mechanism comprises a hydrophobic barrier monomer namely styrene and/or methyl styrene in combination with a monomer selected from one or more unsaturated mono- or di-carboxylic acids.

Another reference, Tocker U.S. Pat. No. 4,282,209 discusses a process for the preparation of insecticide-polymer particles. The insecticide, methomyl, is used to control insects which attack a tobacco, cotton or agricultural crops. Methomyl is dissolved with polymers such as polyamides, urethanes and epoxies to provide long-term residual insecticidal activity.

A second Tocker patent, U.S. Pat. No. 4,235,872, discloses the use of slow-release insecticide microcapsules having a core of methomyl surrounded by a cover of allaromatic, uncrosslinked polyurea. In the arrangement disclosed in this patent, methomyl is used to protect vegetables, field crops and fruit crops.

A sixth reference, Young et al. U.S. Pat. No. 4,198,441, discloses the use of insecticides such as Dursban in a controlled release matrix comprising an organopolysiloxane, a hydrolyzable silane and a hydrolyzable organic titanium.

Additionally, Young et al. U.S. Pat. No. 4,190,680 teaches the use of a controlled release device for insecticides such as Dursban utilizing a hydrolyzable organic titanium compound.

Finally, Von Kohorn et al. U.S. Pat. No. 4,160,335 discloses a mode of dispersing insect control substances by applying stripes to sheets of cellophane. The insect control substance which can include Dursban is placed in a polymer well.

Although the prior art does disclose the use of controlled release agents, none of the references teach the creation of a completely effective exclusion zone. It is desirable to create a zone so as to prevent any contact between the wood structure and insects capable of damaging such structures. An exclusion zone is necessary to protect wood structures for extended periods of time.

Therefore, in view of the above, it is an object of this invention to provide a zone of insecticide to protect wooden structures. Such zone consisting of a long term low volatility barrier and a high volatility short term barrier to protect adjacent soil.

It is a further object of this invention to maintain an exclusion zone for relatively great lengths of time of about 10 to 20 years.

SUMMARY OF THE INVENTION

The present invention provides a delivery system and method for the controlled release of insecticide which lasts for a predetermined period of time at a minimal effective level creating a zone in order to prevent an intrusion of insects such as termites, ants and other boring insects into wooden structures. The method utilizes a controlled release device which comprises a polymer selected from the group consisting of thermoplastic polymers, thermoset polymers, elastomeric polymers and copolymers thereof. By incorporating the insecticides into the polymers, the insecticides can be released at such a rate that they will continue to be effective as toxicants or repellents for insects capable of damaging wood structures for a prolonged period of time while at the same time maintaining sufficient concentrations to prevent insect penetration through the exclusion zone.

According to one aspect of this invention, there is provided a polymeric-carrier delivery system for the controlled release of insecticide comprising spun-bonded polymeric sheeting, and a bonded mixture of polymer and insecticide. The mixture of polymer and insecticide is next bonded to the polymeric sheeting. The sheeting with the bonded mixture of polymer and insecticide is then placed near a wooden structure to provide a means for a slow and relatively constant release of the volatile insecticide in order to create a barrier zone for insects in the soil around a wood structure. The polymers include thermoplastic polymers, thermoset polymers, elastomeric polymers as well as copolymers thereof and the insecticide comprises the family of insecticides known as pyrethrins.

According to another aspect of this invention, an exclusion zone is created by placing an extrusion near the wooden structure to be protected. The extrusion has a polymeric delivery system capable of controlled release of the insecticide. The carrier system maintains a steady and effective concentration of insecticide in the exclusion zone for great lengths of time.

According to another aspect of this invention, a pellet comprising a polymer and insecticide is provided to create and maintain an equilibrium concentration of insecticide for ants, termites and other wood boring insects in an exclusion zone for the wooden structure. The pellet is placed near a wooden structure to treat the soil in order to shield the wooden structure from termites, ants and other boring insects. The pellet can be placed near the structure by a variety of means. Additionally, the pellet can be embedded in a board or even included in a foam. In preferred embodiments the polymers include thermoplastic polymers, thermoset polymers, elastomeric polymers as well as copolymers thereof and the insecticide are pyrethrins.

According to another aspect of this invention, an exclusion zone is create by injecting a hot melt polymeric mixture. The controlled release device comprises one or more pyrethrins and the polymer is selected from the group consisting of thermoplastic polymer, thermoset polymer, elastomeric polymers and copolymers thereof.

According to further aspects of the invention, temperature driven controlled release devices are used to provide the exclusion zones.

According to another aspect of this invention, the controlled release device is used to fumigate structures.

The present invention, together with attendant objects and advantages, will be best understood with reference to the detailed description below read in conjunction with the accompanying drawing.

BRIEF DESCRIPTION OF THE DRAWINGS

FIG. 16 illustrates a hot-melt injection.

FIG. 17 illustrates the spacing of the hot-melt injunction.

FIG. 18 illustrates a plug fumigating cement blocks.

FIG. 19 illustrates a mode of applying plugs to fumigate cement blocks.

DETAILED DESCRIPTION

Figure 1:
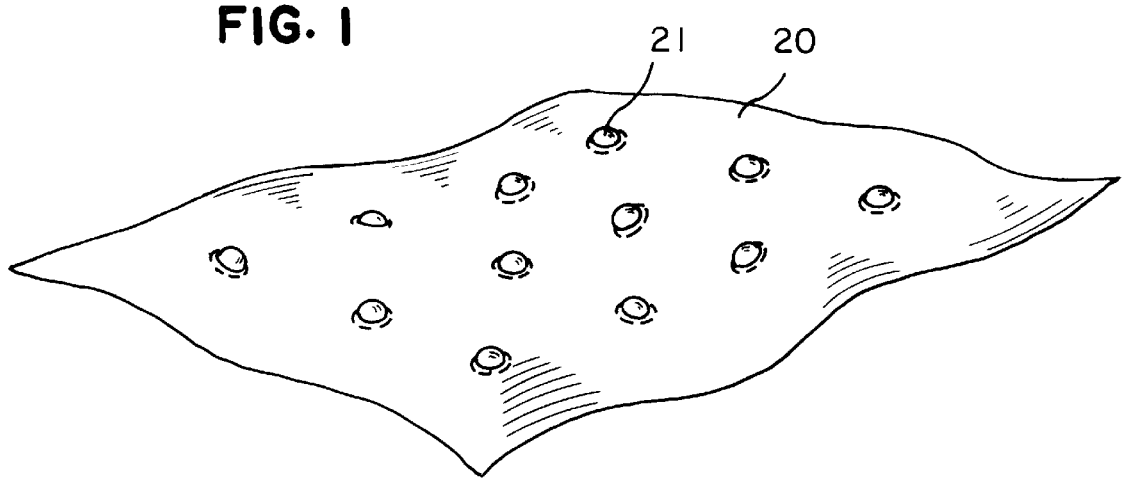
FIG. 1 illustrates a first embodiment of the invention, comprising spun-bonded polymeric sheeting, and a physical melt-bonded mixture of polymer and insecticide, wherein the mixture of polymer and insecticide is bonded in spots to the polymeric sheeting.

It has been found that there is a significant reduction of insects capable of damaging wood structures when an exclusion zone of insecticide is maintained for great lengths of time in the soil surrounding such structures. According to the present invention, the insecticide releases from a controlled release device comprising a polymer matrix system will last for at least 6 years.

A controlled release device refers to a substance that results in controlled and sustained release of an active chemical from its surface or to its surface. The device provides a method for controlled release of the chemical into the surrounding environment. The device releases insecticide at a high rate initially and a lower, steady rate thereafter. This release profile assures that the wooden object becomes protected in a relatively short period of time and that, subsequent to reaching the minimum effective level only the amount of insecticide necessary to replace the degraded insecticide is released. This release profile diminishes potential environmental and health problems of the treatment and reduces the cost of the treatment. A more detailed description of general principles of controlled release devices is given in U.S. patent application Ser. Nos. 06/555,113 filed Nov. 23, 1983 which is a continuation in part of U.S. Ser. No. 06/314,809 and 06/314,810 both filed on Oct. 26, 1981; U.S. Ser. No. 07/086,757, filed Aug. 18, 1987, U.S. Ser. No. 07/072,080 filed Jul. 10, 1987; and U.S. Ser. No. 07/091,918 filed Sep. 1, 1987, the contents of these applications being incorporated herein by reference. Methods for obtaining the release rates are described in patent application Ser. No. 07/303,707 filed on Jan. 30, 1989.

The device provides a long-term solution by releasing the insecticide into the soil at a desired rate to create a zone having the "minimal effective level" of insecticide necessary to prevent insect intrusion. As used in this specification and the appended claims, the term "minimal effective level" is defined to mean the level of insecticide needed in the zone to prevent insects from approaching the zone, the specific level depends on the specific insect and the specific insecticide.

The insecticides used in a preferred embodiments should be U.S. Environmental Protection Agency approved insecticides to kill or repel termites, ants and other boring insects. The insecticide which is presently preferred for use in the present invention are pyrethrins, including tefluthrin, lamdacyhalthrin, cyfluthrin and deltamethrin. It will, however, be recognized by those skilled in the art that other effective insecticides such as isofenphos, fenvalerate, cypermethrin, permethrin and natural pyrethrin can also be used. These are available from a number of commercial sources such as Dow, Mobay, ICI, Velsicol and FMC respectively. A combination of insecticides, or one or more insecticides in combination with other active ingredients such as fungicides is also in accord with this invention.

A first embodiment of the invention, illustrated in FIG. 1, utilizes a polymeric-carrier delivery system for the controlled release of insecticide to generate an exclusion zone. The embodiment comprises spun-bonded polymeric sheeting 20, and a physical melt-bonded mixture of polymer and insecticide (shown as spots 21 in FIGS. 1 and 3–5). The spun-bonded polymeric sheeting 20 can be either a woven or non-woven textile or it can be a polymeric sheet. Such textiles can be obtained from a number of manufacturers such as Reemay, Exxon Fibers and Phillips Fibers. Preferably, the textile is woven or non-woven polypropylene.

The polymer in the melt-bonded mixture can comprise any number of thermoplastic polymers, thermoset polymers, elastomeric polymers or copolymers thereof. The selection of the polymers depends upon the desired release rate, the compatibility of the polymer with the insecticide and upon environmental conditions. By way of example and not intending to limit the scope of this invention, the following polymers can be used: high density polyethylene, low density polyethylene vinyl acetate, urethane, polyester, santoprene silicone, or neoprene. However, the preferred polymers are high density and low density polyethylene. Although the above-mentioned insecticides can be used for best results, the insecticide should ideally comprise chlorpyrifos.

The mixture of polymer and insecticide may be placed on the spun-bonded polymeric sheeting in spots. These spots should be spaced so as to adequately maintain the amount of insecticide above the minimal effective level in an exclusion zone. The minimal effective level is the least amount of insecticide needed in a zone so as to prevent intrusion by insects. Spots 21 in FIGS. 1 and 3–5 are preferably about 0.5 to 1.5 centimeters in diameter, and about 0.5 to 1.5 centimeters in height. The size and shape of the spots will depend upon the user's preference and can be tailored to the job contemplated by the buyer. The spots 21 can be configured in rows with the spacing of the spots preferably being from about 1.5 to about 4 centimeters from adjacent spots. It will be recognized by those skilled in the art that other configurations of spots can also be used depending on the particular application. The insecticide releasing polymeric sheet is placed near or around the wooden structure to create an exclusion zone by the controlled release of insecticide.

A second embodiment of the invention also utilizes a polymeric-carrier delivery system for the controlled release of insecticide comprising spun-bonded polymeric sheeting 20 and a physical melt-bonded mixture of polymer and insecticide. The polymeric sheeting 20 as in the first embodiment can be either woven or non-woven polypropylene upon which is bonded the physical melt-bonded mixture (shown as stripes 22 in FIG. 2). Similarly, the polymers and insecticide described above with respect to the first embodiment may also be used in the embodiment described in this section.

Figure 2:
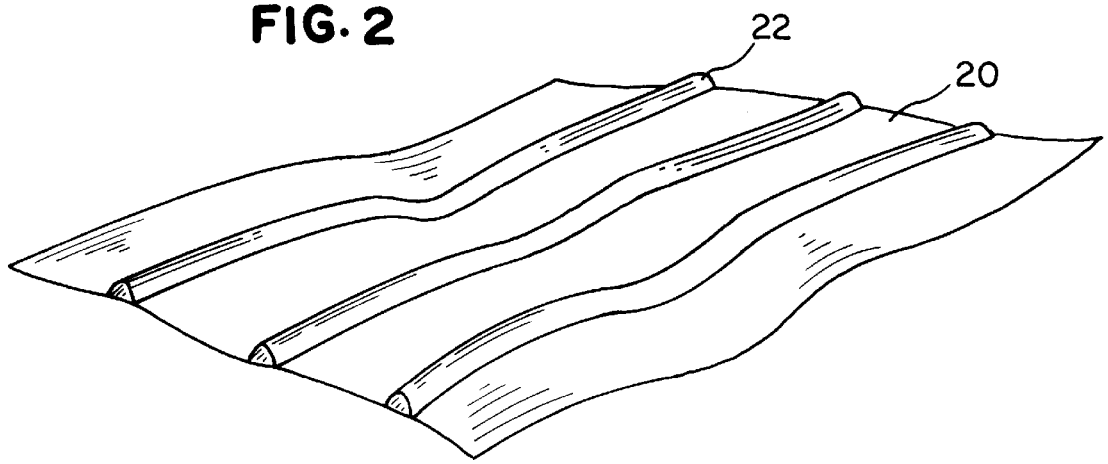
FIG. 2 illustrates a second embodiment of the invention, comprising spun-bonded polymeric sheeting, and a physical melt-bonded mixture of polymer and insecticide, wherein the mixture of polymer and insecticide is bonded in stripes to the polymeric sheeting.

The mixture of polymer and insecticide of the second embodiment may alternatively be placed on spun-bonded polymeric sheeting using extruder systems which provide stripes, e.g., as shown in FIG. 2. The stripes 22 can be about 1 centimeter in height, and about 5 to 15 centimeters apart. Optimally the stripes should be placed about 10 centimeters apart. It is desirable that the stripes should be configured in such an arrangement so as to permit a steady state concentration of insecticide in the exclusion zone after an initial burst of insecticide. After the stripes are applied to the polymeric sheet, the sheet is placed on or near the wooden structure to be protected from insects.

Filler and/or carriers may also be included in all of the embodiments of the invention. The inclusion of the filler and/or carrier permits greater amounts of insecticide to be loaded into the polymer while at the same time assisting in the control of the rate of release of the insecticide. The best results are observed by using carbon black as a filler and/or carrier, but clay or amorphous silica can also be used. Carbon black is preferred because it best serves to stabilize the polymer and increase the possible concentration of insecticide in the polymer while at the same time, permitting control of the polymer matrices' release rate.

If carbon black is utilized, the first step in producing the device is to melt the insecticide and mix it with the carbon black. The melted insecticide adheres to the extremely large surface area of the finely divided carbon black and the mixture is cooled for incorporation in the polymer. Polymers which may be used in a carbon black application are a polyethylene, polypropylene, copolymers or blends of polyethylene and polypropylene, polybutylene, epoxy polymers, polyamides, acrylate-styrene-acrylonitrile, aromatic or unsaturated polyesters, polyurethanes, silicones, or any other suitable polymers or copolymers thereof.

The carbon black-insecticide mixture in the first and second embodiments (or just insecticide, if carbon black is not used) is then mixed with the polymer, preferably polyurethane, in either the molten, powder or liquid stage. Next this mixture is bonded to the polymeric sheeting. In the first and second embodiments of the invention, the polymer and insecticide are melt-bonded to the polymeric sheeting.

Another mode of bonding the mixture of polymer and insecticide to the polymeric sheeting is by "through-injection molding," a technique which is known in the art. In "through-injection molding," molten material is injected from a heated nozzle through a porous web and into a mold. The molten material flows through the web under pressure and is solidified in the mold. While the molten material is being injected, the porous web allows air to escape, but it also retains the molten mass under pressure until it has cooled.

A different method of bonding the mixture of polymer and insecticide to the polymeric sheeting is by placing a melted mixture of polymer and insecticide on the spun-bonded polymeric sheeting. If the mixture is melted, it must be allowed to cool, cure and solidify. As used hereinafter, "a melted mixture of polymer and insecticide" is intended to indicate that the polymer is either melted or already in the liquid stage. The insecticide may also be melted or contained in a slurry solution, depending on its melting point. A "melted mixture of polymer and insecticide" can also contain carbon black or other additives which do not melt but flow with the melted polymer/insecticide mass.

The first and second embodiments of the invention should provide release rates sufficient to maintain an effective insecticide concentration in the exclusion zone to kill or repel insects but at sufficiently slow rates to maintain an effective concentration for an extended period of time. Overall, a preferred composition for the first and second embodiments of the invention comprises from about 70 to about 95 parts by weight of carrier polymer, from 0 to about 15 parts by weight of carbon black, and from about 5 to about 30 parts by weight of insecticide. The design considerations of the controlled release devices vary according to such factors as user preference and geographic conditions. The steady state release rate of the polymeric delivery system of these two embodiments after the initial burst of insecticide can be maintained for at least 6 years as a barrier to insects such as ants and termites. However, the equilibrium concentration of this embodiment can easily be adjusted to meet the specific needs of each user.

Optionally, the embodiments shown in FIGS. 1–5 may comprise an insecticide-impervious sheet (not shown) such as a metallized foil. The metallized foil or an extruded sheet of a polymer is laminated to one side of the spun-bonded polymeric sheeting in order to direct the flow of insecticide.

Figure 3:
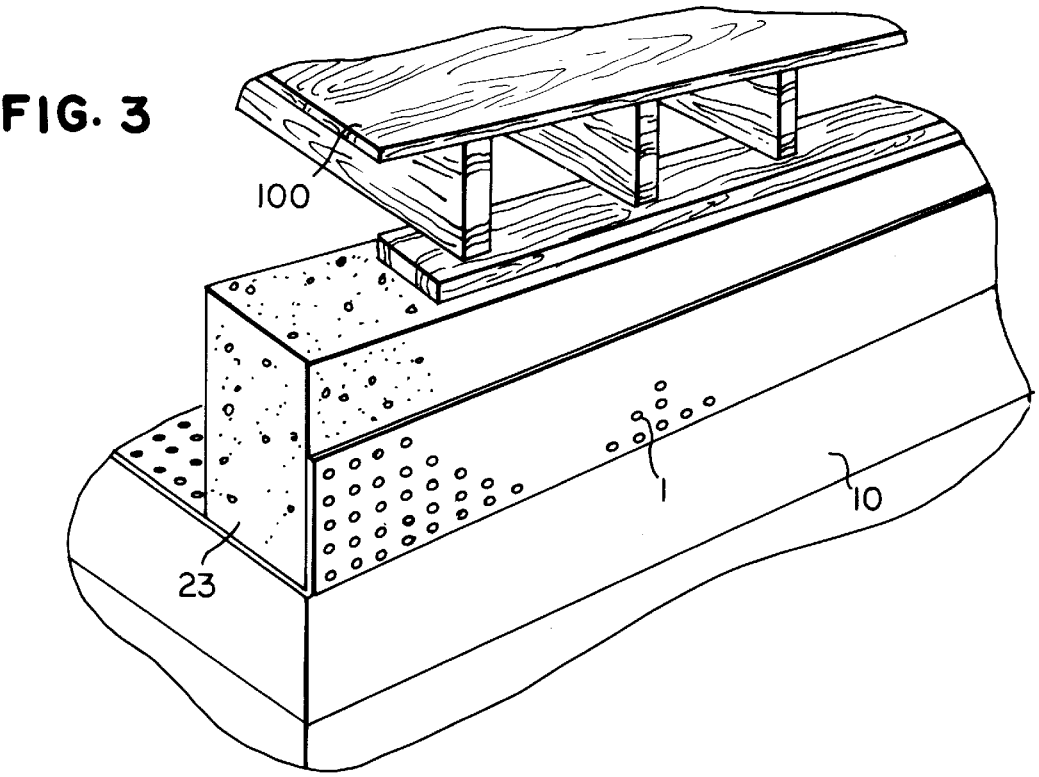
FIG. 3 illustrates a first manner of using the embodiments of the invention shown in FIGS. 1 and 2 and the exclusion zone created by the release of insecticide.
Figure 4:
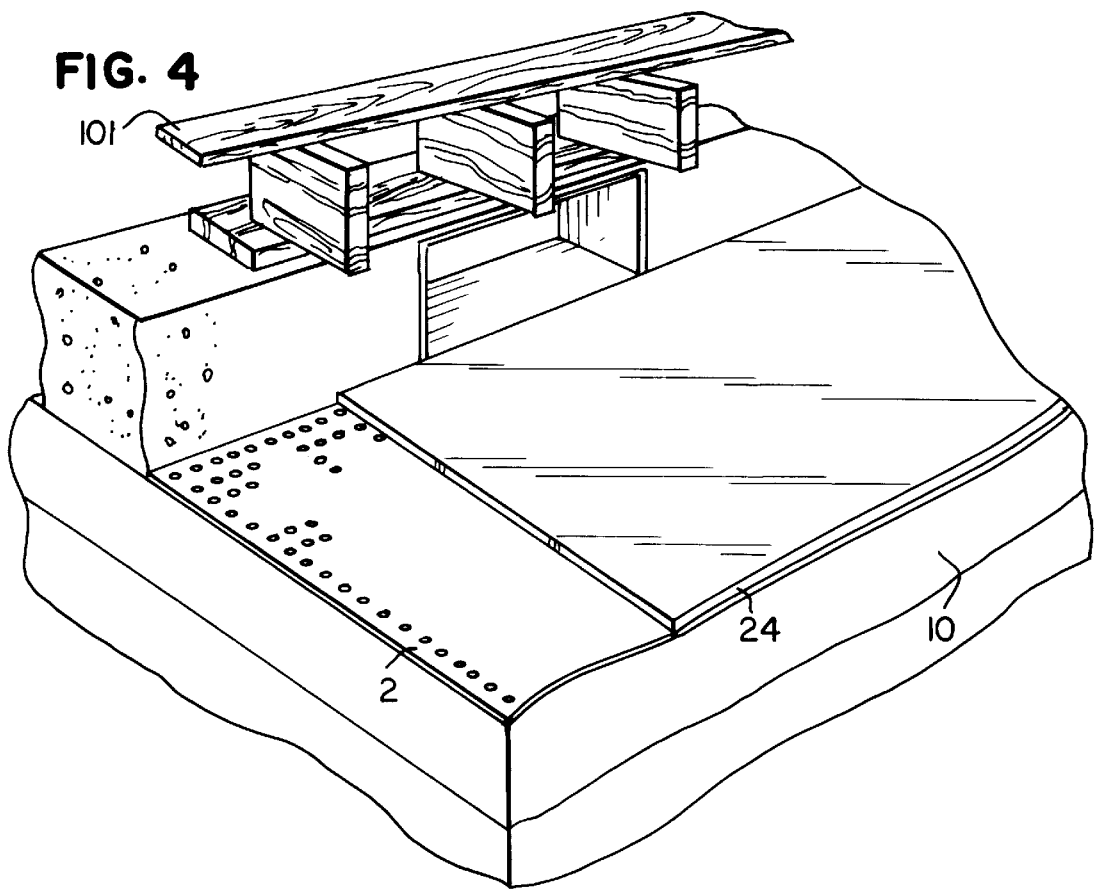
FIG. 4 illustrates a second manner of using the first and second embodiments of the invention to create an exclusion zone.
Figure 5:
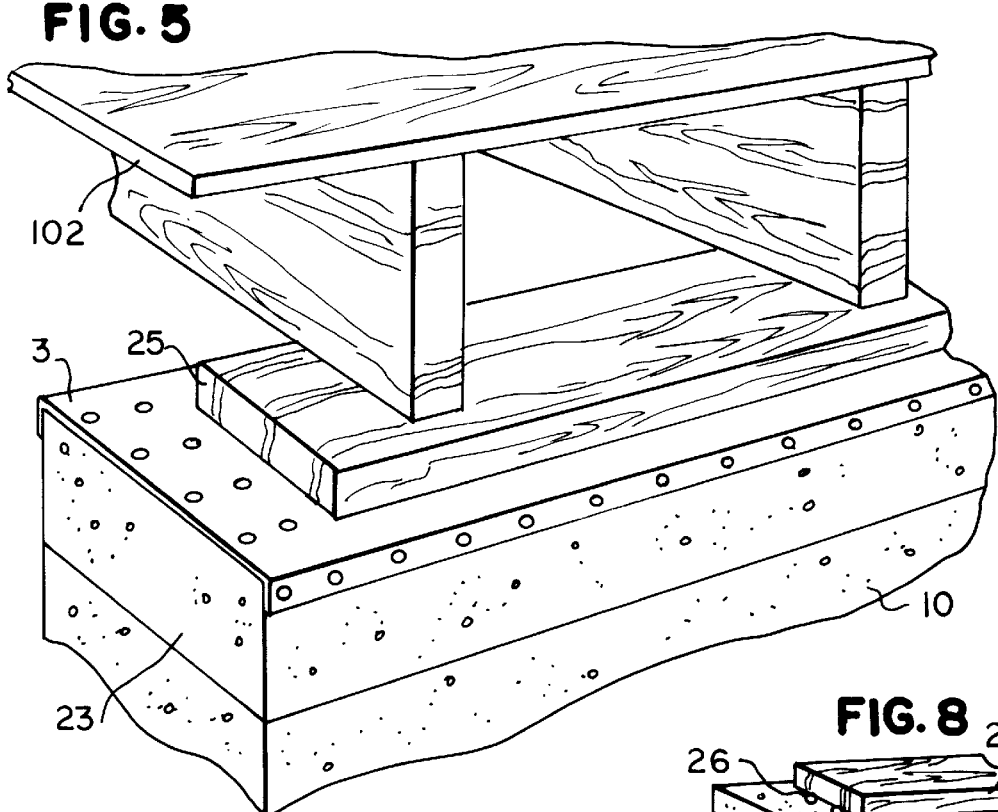
FIG. 5 illustrates a third manner of using the embodiments of the invention shown in FIGS. 1 and 2 creating an exclusion zone.

Once made, the polymeric-carrier delivery systems of the first and second embodiments are placed near the structure desired to be protected from insects. FIGS. 3–5 illustrate various applications of either the spotted or striped sheet embodiments of the invention. The FIG. 1 configuration is shown in FIGS. 3–5, but it is understood that the FIG. 2 configuration, or other configurations can work as well.

In FIG. 3, the polymeric-carrier delivery system 1 is placed under and alongside a concrete foundation 23 of a wooden structure 100 creating an exclusion zone 10 to protect the structure from termites, ants and other boring insects.

In FIG. 4, the polymeric-carrier delivery system 2 is placed under a structural member 24, such as a porch, patio, sidewalk, or under a basement foundation beside the wooden structure 101 to provide an exclusion zone 10.

In FIG. 5, the polymeric-carrier delivery system 3 is placed over and on the sides of the concrete foundation 23 of a wooden structure 102, but under the wooden portion 25 of the structure to create an exclusion zone.

Figure 6:
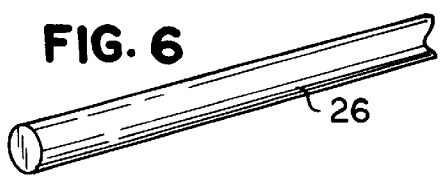
FIG. 6 illustrates a third embodiment of the invention, in the form of a cylindrical extrusion.
Figure 7:
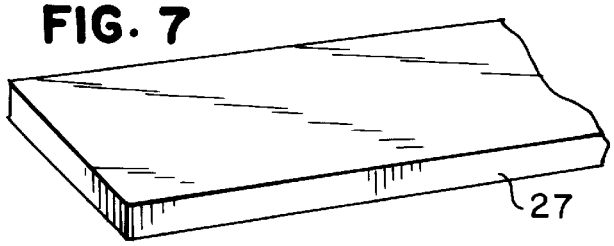
FIG. 7 illustrates a fourth embodiment of the invention, in the form of a flat strip extrusion.

Another embodiment of the invention is illustrated in FIGS. 6 and 7. This embodiment pertains to extrusions, such as extruded flexible cylinders 26 and extruded flexible flat strips 27 shown respectively in FIGS. 6 and 7. A wide variety of polymers which can be classified into four broad subgroups can be utilized. The groups include thermoplastic polymers, thermoset polymers, elastomeric polymers and copolymers of the three groups named above. By way of example, some polymers which can be used form the four groups are: high density polyethylene, low density polyethylene, EVA, vinyl acetate, urethane, polyester, santoprene, silicone, neoprene and polyisoprene. The preferred insecticide is chlorpyrifos although the insecticides described above can be used. Carbon black may also be added.

Cylinders preferably have a size ranging from about 5 to about 15 millimeters in diameter, but most preferably about 10 millimeters in diameter for the optimal steady state delivery of insecticide into the exclusion zone. Flat strips should preferably have a thickness of from about 1 to 6 millimeters and a width of from about 5 to 15 millimeters. It, however, should be noted that both cylinders and flat strips can be designed to meet the varying conditions encountered by user.

Overall, in order to maintain an equilibrium concentration of insecticide in the exclusion zone for an extended period of time, the composition of this embodiment of the invention, should comprise from about 70 to about 95 parts by weight of polymer, from about 0 to about 30 parts weight of carbon black, and from about 5 to about 30 parts by weight of insecticide. The composition of the extrusion can, however, be tailored to the specific needs of the user. It is estimated that the exclusion zone can be maintained for at least 6 years for a cylinder and likewise for flat strips.

Figure 8:
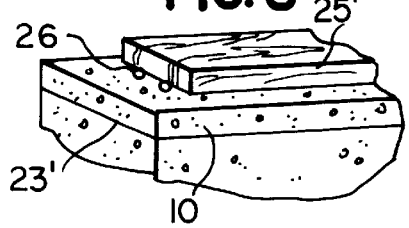
FIG. 8 illustrates a manner of creating an exclusion zone using the embodiment of the invention shown in FIG. 6.

The extrusions can be positioned in a variety of positions to create exclusion zones. FIG. 8 illustrates a manner of using the extrusion shown in FIG. 6. One or more flexible cylinders 26 are placed between the concrete foundation 23' and the wooden portion 25' of the structure. The flexible cylinders 26 release insecticide at a controlled rate to create an exclusion zone. An advantage of this configuration is that flexible cylinders 26 can be placed under a structure that has already been built. Similarly, in a manner not shown, the flexible cylinders can be placed vertically into the ground as opposed to horizontally. As will be recognized by those skilled in the art, the extrusions may have other suitable shapes and be placed in any suitable position depending upon the particular use contemplated.

Figure 9:
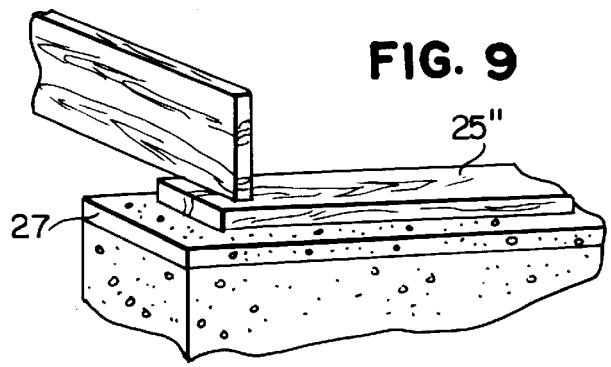
FIG. 9 illustrates a manner of using the embodiment of the invention shown in FIG. 7 to create an exclusion zone.

FIG. 9 illustrates a manner of using the flexible flat strip extrusion shown in FIG. 7. One or more flexible flat strips 27 create an exclusion zone by being placed between or alongside the concrete foundation 23" and the wooden portion 25" of the structure. The flexible flat strips 27 can also be placed vertically alongside a wall in an embodiment not illustrated in the drawings. Again, any suitable placement of the flat strips is considered as being within the scope of the invention.

The controlled release of insecticide can also be conveniently achieved by using pellets as illustrated in the embodiments shown in FIGS. 10 through 13. The pellet 13 comprises polymer, insecticide and preferably also includes a filler. Various polymers can be used in this embodiment. They can comprise polymers of four subgroups consisting of thermoplastic polymers, thermoset polymers, elastomeric polymers and copolymers thereof. Polymer selection from these four subgroups depends upon design considerations with the preferable polymer being either high density polyethylene or low density polyethylene. In turn, the insecticide preferably comprises tefluthrin, but the following insecticides can also be used: isofenphos, fenvalerate, cypermethrin, permethrin and other pyrethrins. For optimal results, a carrier such as carbon black, can also be incorporated into the mixture.

The pellet 31 releases insecticide at a controlled rate for an extended period of time in order to establish an exclusion zone. The composition for such a pellet needed for the maintenance of a zone in the soil is from about 70 to about 95 parts by weight of polymer, from about 0 to about 30 parts by weight of carbon black, and from about 5 to about 30 parts by weight of insecticide. Ultimately, the compositions of the pellet depend upon user preference.

The pellets can be any convenient size depending upon the intended use, such as 1 to 25 millimeters in diameter (or width and thickness, if rectangular) by 2 to 20 centimeters or more in length. Furthermore, in order to fit specific user needs, the dimension of the pellets and the concentrations of the insecticide can easily be adjusted. However, an exclusion zone can be maintained for at least 6 years.

Figure 10:
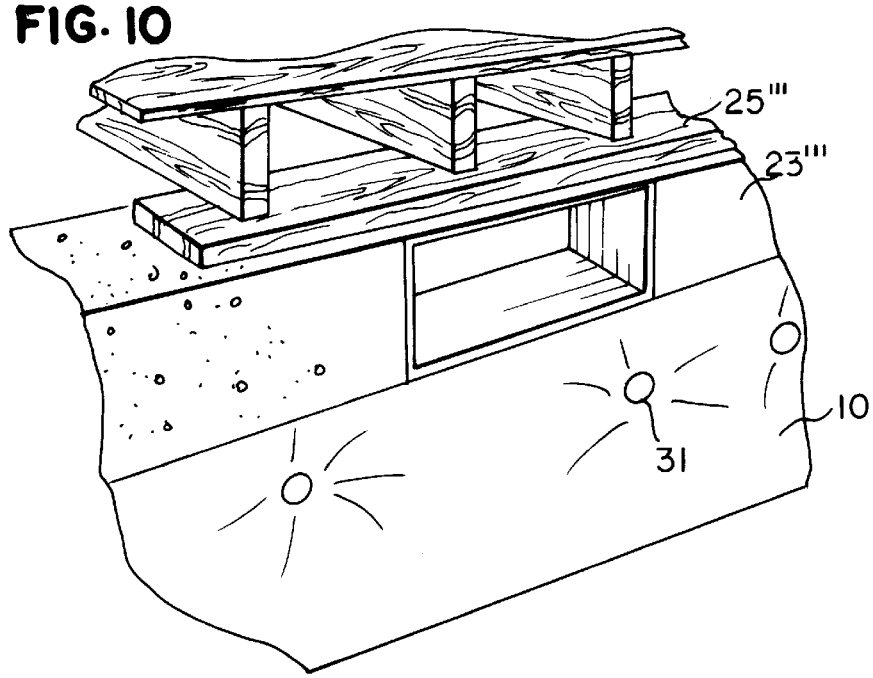
FIG. 10 illustrates another embodiment of the invention in the form of pellets wherein the pellets are being inserted into the ground near a wooden structure.
Figure 11:
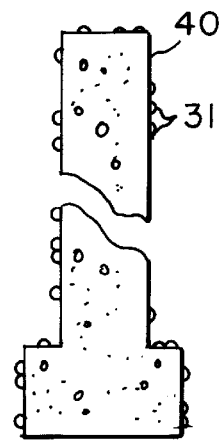
FIG. 11 illustrates a cross-sectional view of pellets placed on a surface.

Additional, pellets 31 have the advantage that they can be conveniently placed most anywhere. The pellets of this embodiment of the invention are shown in FIG. 10. A pellet 31 is inserted near a wooden structure 25. The pellets as illustrated in FIG. 10 can be placed under a cement foundation 23''' or they can be placed directly under the wood structure (not illustrated) so as to permit the creation of a zone 10 surrounding the wooden structure 25''' to exclude insects capable of damaging such structures. FIG. 11 shows a cross-sectional view of pellets 31 inserted on a surface 40.

Figure 12:
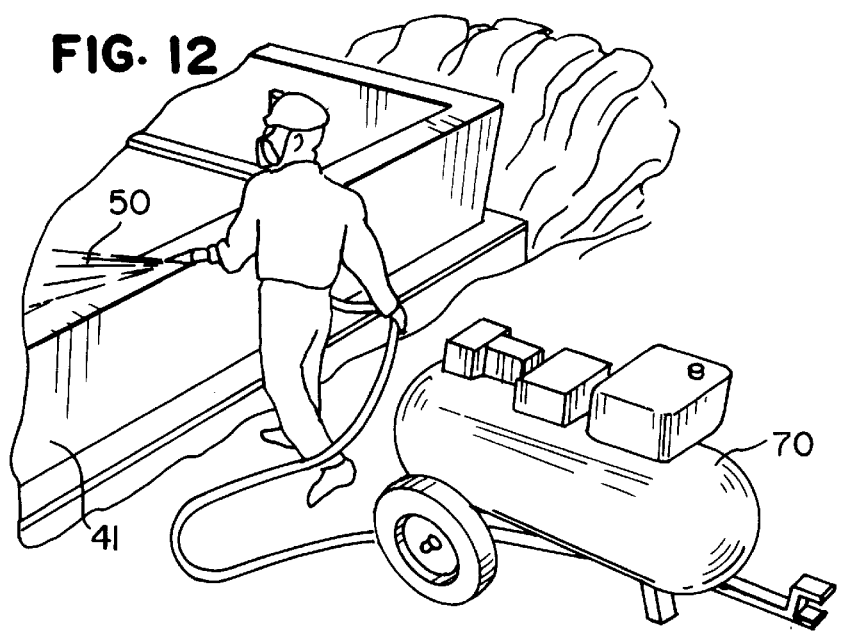
FIG. 12 illustrates the application of pellets to a concrete structure utilizing foam.
Figure 13:
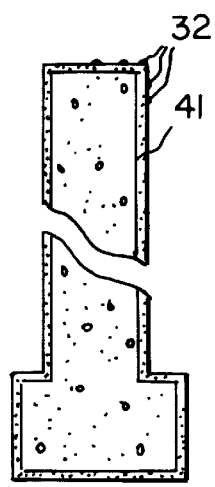
FIG. 13 illustrates a cross-sectional view of a concrete foundation after foam has been applied.
Figure 15:
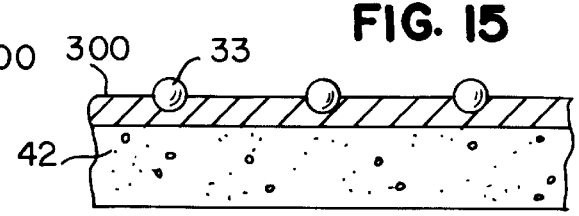
FIG. 15 illustrates a board containing pellets being applied to a concrete foundation.

Pellets are easily applied to a wide variety of uses. FIG. 12 illustrates pellets sprayed onto a concrete structure 41. FIG. 15 illustrates treating a surface by placing pellets 33 on preformed boards 300.

Pellets 32 are applied onto a surface 41 such as soil or concrete via a foam 50 as illustrated in FIG. 12. The pellets are first incorporated into a foam in a manner known in the art. The foam 50 containing the fine pellets is then sprayed as illustrated onto the surface 41 via a motorized sprayer 70 in FIG. 12 so as to provide a protective coating for the surface. The pellets then release the insecticide to create a protective barrier in the soil to protect the wood from harmful insects. For best results, the foam 50 is comprised of polyurethane. It is also possible to use silicone, polyester, or polyvinyl acetate. The pellets 32 can vary in size depending upon the foam thickness and the desired concentration of insecticide in the exclusion zone. The thickness of the foam to be applied to a surface can vary according to user's preference. The exclusion zone can be maintained for at least 6 years. In addition to being used as a carrier for insecticide, the foam also cures cement and acts as an insulator.

Figure 14:
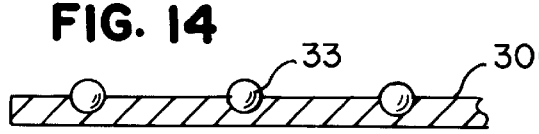
FIG. 14 illustrates pellets set on a board.

A preformed board with embedded pellets 33 cal also be utilized as an embodiment of this invention as illustrated in FIG. 14. This board 300 can be made of any type of material which can suitably hold the pellets 33. Preferably, the board is comprised of styrofoam which is registered as a Dow trademark. The board can be applied in any variety of fashions and can also work as an insulating device. One manner of application is illustrated in FIG. 15, where the board 300 with pellets 33 is placed above a concrete surface 42. The embedded pellets are regularly spaced with the spacing being specified by the devised amount of insecticide.

In another embodiment as shown in FIGS. 16 and 17, the controlled release device comprising the polymer matrix and insecticide can be applied via a hot melt. This embodiment is designed to met the needs of structures already in place. As stated above, the polymer matrix can comprise any of the four above-named polymer groups. Similarly, any of the above-named insecticides can be utilized. However, it is preferable to use high or low density polyethylene with either a pyrethrin. Although tailored to the user, the concentrations of the various substances in the hot-melt application should range from about 70 to about 95 for the polymer, from about 5 to about 30 for the insecticide and from about 0 to about 30 for filler/carrier for optimal results.

FIG. 16 shows hot melt 50 being injected by a syringe 400 into the ground near a concrete foundation 43. The concrete structure 43 supports a wooden structure 250. FIG. 17 shows the spacing between the hot melt 50 which has already been injected into the ground.

In another embodiment, FIGS. 18 and 19 illustrate the use of insecticide to fumigate a structure 500. By injecting or placing the controlled release device in or near a structure which can be fumigated, the insecticide released from the controlled release device can vaporize thereby fumigating the structure. FIG. 18 illustrates the use of plugs 34 to fumigate a structure 500 made of building blocks 502. Similarly, FIG. 19 illustrates a mode of applying the controlled release device by using a drill 800 to bore a hole 700 into a cement slab 900. Once inserted, the plug is able to fumigate the structure.

Currently Preferred Embodiment

The currently preferred product of employing the present invention comprises a polymer sheet, having thickness preferably in the range from about 1/16 to 1/8 inch and a low vapor pressure insecticide, preferably permethrin. The preferred polymers are polyurethane and polyethylene. Adjacent to and, preferably attached to the polymer sheet are additional controlled release devices. These devices are preferably in the form of elongated bars but can be in any suitable form, including pellets.

These additional devices preferably have a polymeric matrix made of EVA or, polyethylene and contain a higher vapor pressure pyrethrin such as tefluthrin. The sheet provides long term chemical contact protection. The additional devices associated with the sheet release the insecticide at a higher rate to provide a chemical barrier in the adjacent structure or soil.

This approach can also be used, for example, for sill plates. A controlled release strip of low vapor insecticide in a polymer matrix has associated therewith additional controlled release devices employing a higher vapor pressure insecticide. The strip acts as a contact protection against entry of insects and the additional controlled release devices release insecticides into concrete or wood to form a barrier in the concrete or wood to entry of insects.

The following examples are provided by way of explanation. As such, these examples are not view as limiting the scope of the invention as defined by the appended claims.

EXAMPLE 1

Experiments were conducted to determine the release rates of insecticides. The experimental approach involved an evaluation of polymer compatibility with chlorpyrifos. Furthermore, there was an analysis of release rates for the individual carrier delivery systems. Loading rates for the insecticide were held to either 5% or 10%, depending on polymer. Release rates were determined for all devices at 50° C.

Polymers evaluated included low melt polyethylene, polyurethane, two epoxies, silicone rubber, and a low melt polyethylene high in waxes to reduce thermal decomposition of the chlorpyrifos. Studies indicated that excessive thermal decomposition of the chlorpyrifos occurred at temperatures in excess of approximately 240° C.; thus, polymer selection was restricted to formulations not requiring excessive heat processing.

Table 1 provides a summary of the results from these studies. Overall, polymer compatibility with chlorpyrifos did not appear to present a problem with the loading rates employed. There was some loss of physical integrity of the polyurethane polymer employed, however, the other polymer systems exhibited no visible degradation at 50° C. Release rates ranged from 10 μg/cm²/da for the silicone rubber, to 0.3 μg/cm²/da for Epoxy B.

TABLE 1

Polymer Formulations and Release Rates for Candidate Systems Employing Chlorpyrifos.

| Polymer Class | Chlorpyrifos Content (%) | Release Rate (μg/cm²/da)[a] |
|---|---|---|
| Polyurethane | 5 | 2.1 ± 1.4[b] |
| Epoxy A | 5 | <0.1 |
| Silicone | 5 | 10.3 ± 3.5 |
| Urethane | 10 | 1.0 ± 0.3 |
| Epoxy B | 10 | 0.3 ± 0.1 |
| PE + Wax | 10 | 1.9 ± 0.3 |

[a]Release rates performed at 50° C.
[b]Material exhibited excessive cracking at elevated temperature Using the data provided in Table 1, an estimated product longevity can be approximated. Assuming a device wt. of 0.5 gm, with 10% load, then 50 mg of chlorpyrifos is available for release. Thus, for a polymer system having an area of 4 cm², and a release rate of 1 μg/cm²/da, there is sufficient insecticide to last 30 years at elevated temperature. These rather simple calculations indicate that a variety of insecticidal products are possible.

EXAMPLE 2

Studies were also conducted with similar polymer systems as in Example 1 but with 80% pure pyrethrin. Release rates at 40° C. are provided in Table 2. The release rates were highest for urethane and silicone and lowest for the epoxies. Substantial variability in release rates were encountered and appropriate binders will need to be evaluated.

TABLE 2

Polymer Formulations and Release Rates for Candidate Systems Employing Pyrethrin I.

| Polymer Class | Pyrethrin I Content (%) | Release Rate (μg/cm²/da)[a] |
|---|---|---|
| Epoxy A | 10 | 0.5 ± 0.2 |
| Silicone | 10 | 21.2 ± 5.4 |
| Urethane | 10 | 15.7 ± 7.1 |
| Epoxy B | 10 | 0.2 ± 0.1 |

[a]Release rates performed at 40° C.

From the data above, simply calculations can be performed to determine the possible life of the insecticide systems. As stated in Example 1, there are many variable which can alter the lifetime of an exclusion zone.

EXAMPLE 3

The following controlled release devices were made and tested to obtain their release rates. The devices were made as follows. All devices, except for those employing S-113 urethane, were injection molded into a thin sheet about ⅛ inch thick. The device employing S-113 urethane was cast, a method typically used for thermoset polymers. All thermoplastics were formulated using sufficient amount of carbon black to carry pesticides. All thermoplastic polymers were formulated with 10 percent pesticide, 3 or 7 percent carbon black to absorb liquid pesticide and 87 to 83 percent by weight of polymer. Specifically, devices made from thermoplastic polymers and deltamethrin and lambdacyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast, using a spin caster into a ⅛ inch thick sheet and heated at about 60° C. for about 40 to 60 minutes to cure the cast sheet.

On inch squares were then cut from the thin sheets that were injection molded or cast and the squares were tested for release rates. The following release rates were obtained:

| Pesticide | Polymer | Release Rate |
|---|---|---|
| Deltamethrin | S-113 urethane | 25.2 μg/cm2/day |
| | Aromatic 80A | 16.8 μg/cm2/day |
| | pellethane 2102-80A | 8.8 μg/cm2/day |
| | pellethane 2102-55D | 8.0 μg/cm2/day |
| | Alipmtic PS-49-100 | 7.2 μg/cm2/day |
| Cypermethrin | polyurethane 3100 | 0.4 μg/cm2/day |
| | polyurethane 2200 | 0.7 μg/cm2/day |
| | EVA 763 | 27.3 μg/cm2/day |
| | Polyethylene MA7800 | 4.6 μg/cm2/day |
| Lambdacyhalothrin | polyurethane 3100 | 0.7 μg/cm2/day |
| | polyurethane 2200 | 2.0 μg/cm2/day |
| | EVA 763 | 20.6 μg/cm2/day |
| | Polyethylene MA78000 | 5.2 μg/cm2/day |
| Tefluthrin | polyurethane 3100 | 6.4 μg/cm2/day |
| | polyurethane 2200 | 25.0 μg/cm2/day |
| | EVA 763 | 40.4 μg/cm2/day |
| | Polyethylene MA78000 | 27.0 μg/cm2/day |
| Permethrin | polyurethane 3100 | 1.4 μg/cm2/day |
| | polyurethane 2200 | 1.3 μg/cm2/day |
| | EVA 763 | 28.5 μg/cm2/day |
| | Polyethylene MA78000 | 4.0 μg/cm2/day |

From the foregoing description one skilled in the art can easily ascertain the essential characteristics of this invention and without department from the spirit and scope of the invention thereof can make changes and modifications of the invention in order to adapt it to the various usages and conditions. It is intended that the scope of the invention be defined by the following claims including all equivalents which are intended to define this invention.

We claim:

1. A method of preventing termites and other boring insects from damaging a wooden structure by creating a controlled release barrier around said wooden structure to prevent insects from penetrating said wooden structure without being killed, said method comprising the following steps:

a. mixing an insecticide selected from a group consisting of isofenphos, fenvalerate, cypermethrin, permethrin or pyrethrin with a polymer to form a mixture;

b. forming the mixture into a shaped controlled release barrier;

c. placing a controlled release barrier around the wooden structure; and, d. allowing the insecticide to release onto the surface of the barrier to create an exclusion zone, said barrier entirely preventing penetration of the barrier by boring insect.

2. The method of claim 1 wherein the step of mixing an insecticide with a polymer includes mixing an insecticide selected from the group consisting of isofenphos, fenvalerate, cypermethrin, permethrin or pyrethrin.

3. The method of claim 2 wherein the step of mixing includes carbon black.

4. A method of creating and maintaining an exclusion zone around a wooden structure for exclusion of termites and other boring insects by creating a controlled release barrier around said wooden structure to prevent crawling and soil borne insects from infesting and damaging the wooden structure, said method comprising the following steps:

a. incorporating an insecticide into a polymer to form a controlled release device, the amount of the insecticide being sufficient to provide a minimal effective level in said barrier for a predetermined time period;

b. forming the controlled release device;

c. placing controlled release device at entry points to the wooden structure; and, d. allowing the insecticide to release from said device to create said barrier, said barrier entirely preventing insects from penetrating said wooden structure.

5. The method of claim 4 wherein the step of forming comprises extruding.

6. The method of claim 5 wherein the step of mixing comprises mixing a polymer selected from the group consisting of thermoplastic polymers, thermoset polymers, elastomeric polymers and copolymers thereof.

7. The method of claim 6 wherein the step of mixing comprises mixing an insecticide comprising chlorpyrifos with a polymer comprising polyethylene.

8. The method of claim 7 wherein the step of placing comprises incorporating the pellets in a foam and spraying the foam with the pellets onto a surface.

9. The method of claim 8 wherein the foam comprises polyurethane.

10. The method of claim 8 wherein the pellet is inserted into a styrofoam board.

11. A method for creating a barrier for creating and maintaining an exclusion zone around a wooden structure entirely to prevent termites and other boring insects from damaging the wooden structure, said method comprising:

a. incorporating an insecticide into a polymer to form a mixture;

b. melting the mixture;

c. injecting the mixture to produce a controlled release device;

d. placing said device at entry points to said wooden structure;

e. allowing the insecticide to continuously release to entirely prevent insects from crossing said barrier.

\* \* \* \* \*